US012653625B2

(12) United States Patent     (10) Patent No.:   US 12,653,625 B2

Kemper et al.           (45) Date of Patent:     Jun. 16, 2026

(54) SURGICAL REFERENCE BODY FOR REFERENCING A PATIENT'S ANATOMY DURING SURGERY

(71) Applicant: Stryker European Operations Limited, Carrigtwohill (IE)

(72) Inventors: Jakob Kemper, Heemstede (NL); Lars Metz, Kiel (DE); Ulrich Hoffmann, Breisach (DE); Fabian Huegle, March (DE); Bernd Simon, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 172 days.

(21) Appl. No.: 18/568,353

(22) PCT Filed: Jun. 8, 2021

(86) PCT No.: PCT/IB2021/055021

§ 371 (c)(1),
(2) Date: Dec. 8, 2023

(87) PCT Pub. No.: WO2022/259019

PCT Pub. Date: Dec. 15, 2022

(65) Prior Publication Data

US 2024/0285350 A1     Aug. 29, 2024

(51) Int. Cl.
*A61B 34/20*       (2016.01)

(52) U.S. Cl.
CPC ...... *A61B 34/20* (2016.02); *A61B 2034/2055* (2016.02); *A61B 2034/2065* (2016.02)

(58) Field of Classification Search
CPC ...... A61B 17/1703; A61B 2017/00951; A61B 2034/2055; A61B 2034/2065; A61B 2090/376; A61B 2090/3966; A61B 2090/3983; A61B 34/20; A61B 90/39

See application file for complete search history.

(56) References Cited

U.S. PATENT DOCUMENTS

| | | | | | |
|---|---|---|---|---|---|
| 2005/0277832 | A1* | 12/2005 | Foley | ................. | A61B 17/7083 |
| | | | | | 600/426 |
| 2010/0046718 | A1 | 2/2010 | Weiser et al. | | |
| 2015/0078535 | A1* | 3/2015 | DeSena | .................. | A61B 90/39 |
| | | | | | 378/204 |
| 2019/0133693 | A1* | 5/2019 | Mahfouz | .................. | A61B 6/12 |

FOREIGN PATENT DOCUMENTS

| | | |
|---|---|---|
| JP | 2018-532484 A | 11/2018 |
| JP | 2019-500185 A | 1/2019 |
| JP | 2020-527380 A | 9/2020 |
| WO | 2017064290 A1 | 4/2017 |
| WO | 2017-106357 A1 | 6/2017 |
| WO | 2018236936 A1 | 12/2018 |
| WO | 2019211741 A1 | 11/2019 |

OTHER PUBLICATIONS

International Search Report including Written Opinion for Application No. PCT/IB2021/055021 mailed Apr. 29, 2022, pp. 1-21.

* cited by examiner

*Primary Examiner* — Mark D Remaly

(74) *Attorney, Agent, or Firm* — Lerner David LLP

(57) ABSTRACT

Surgical reference body, surgical guiding device, and surgical tracking system, and in particular to a surgical reference body, a surgical guiding device, and a surgical tracking system allowing an improved localization of surgical components.

16 Claims, 8 Drawing Sheets

$60=61+62(+63)$
$65=66+67(+68)$

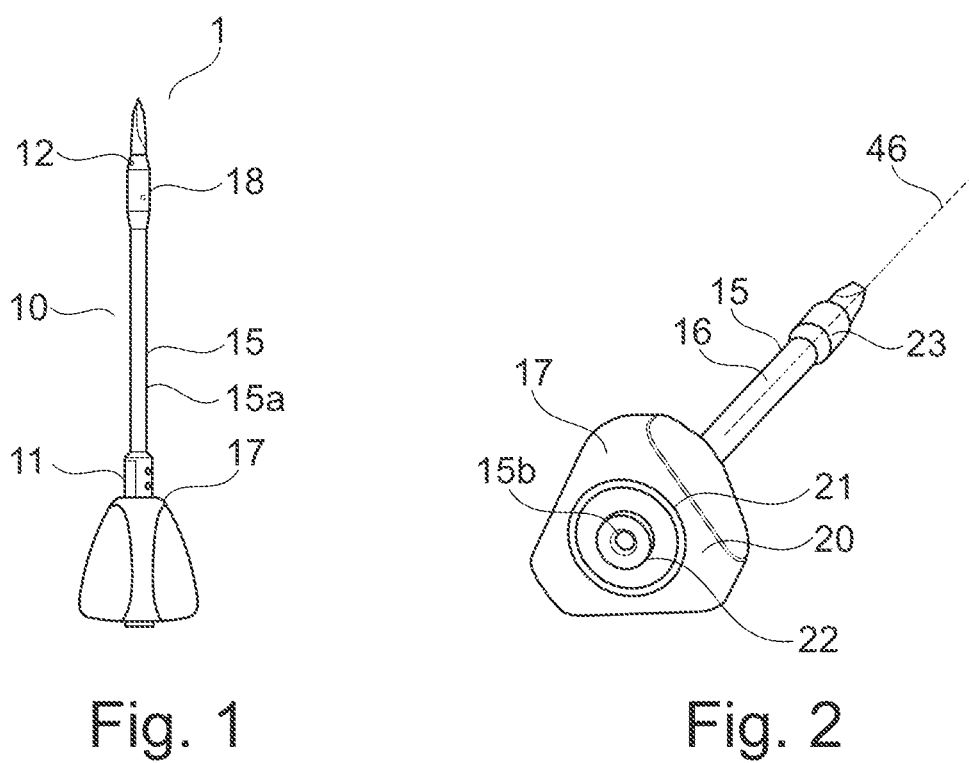
Fig. 1                    Fig. 2
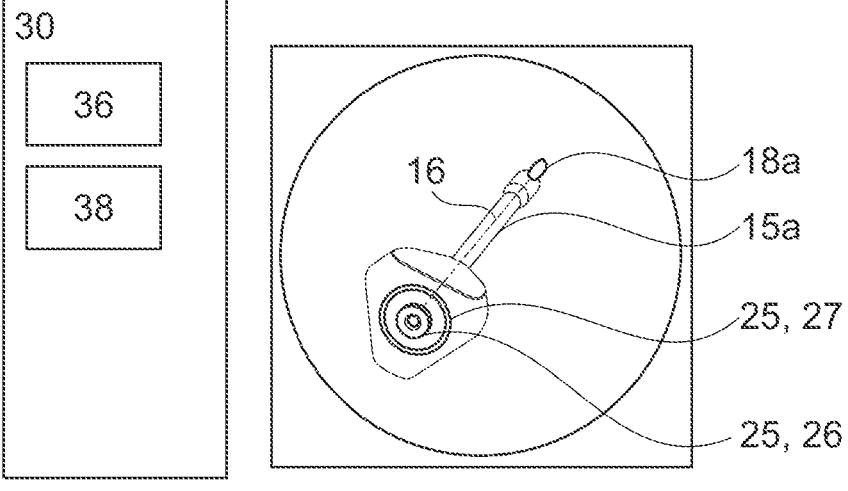
Fig. 3

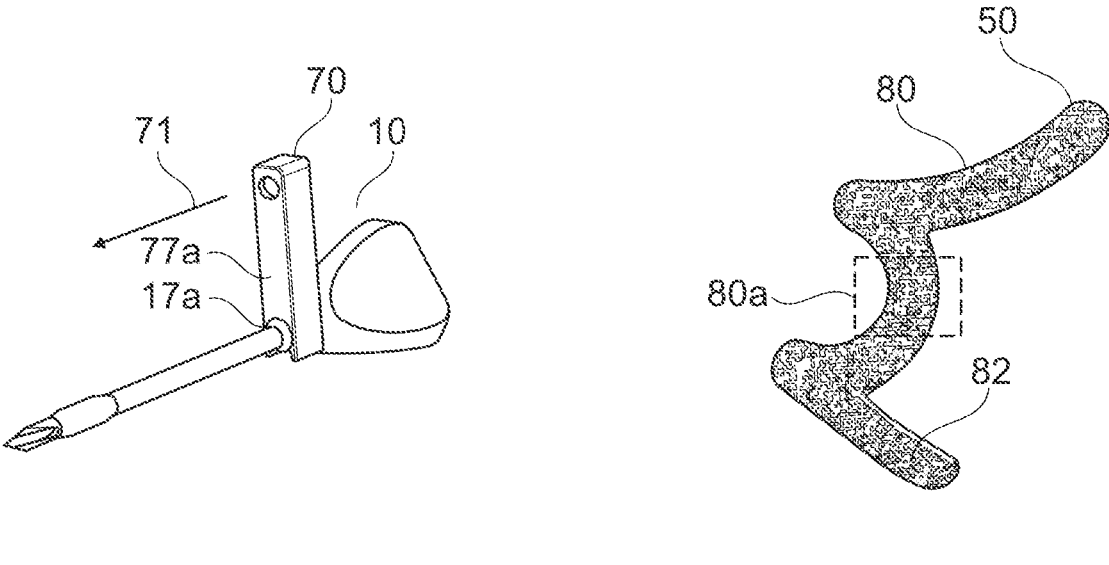
Fig. 6                    Fig. 7
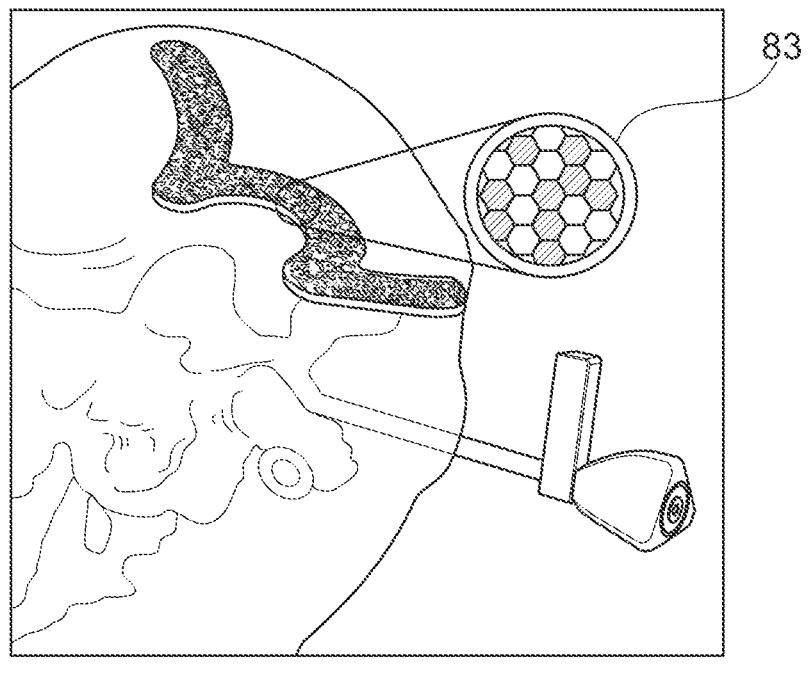
Fig. 8

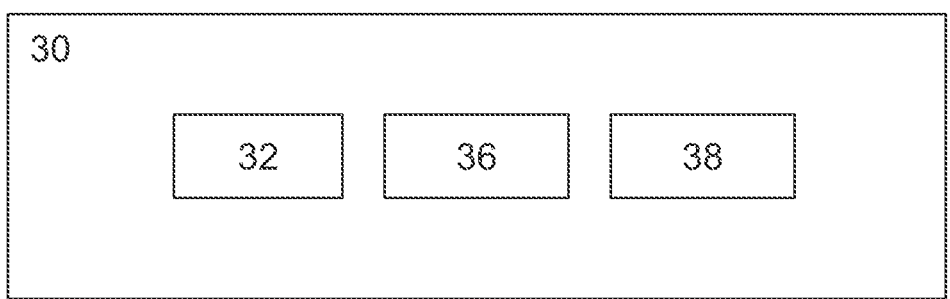
Fig. 9
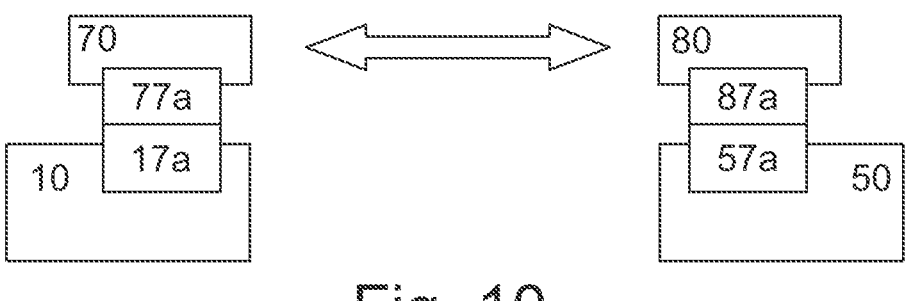
Fig. 10
Fig. 11

$60=61+62(+63)$
$65=66+67(+68)$

60=61+62(+63)

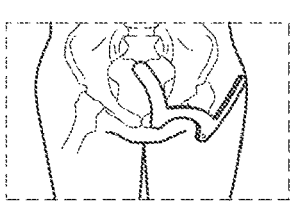
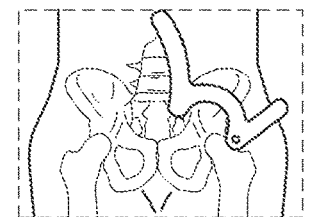
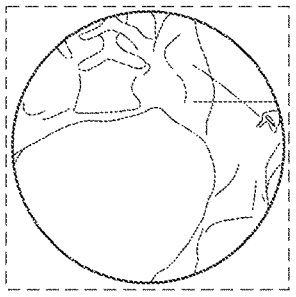
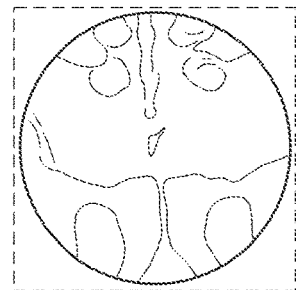
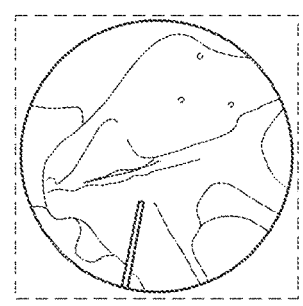
Inlet          Outlet          Lateral
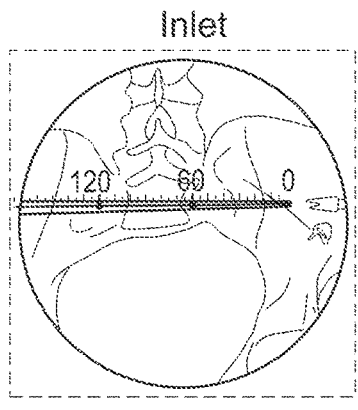
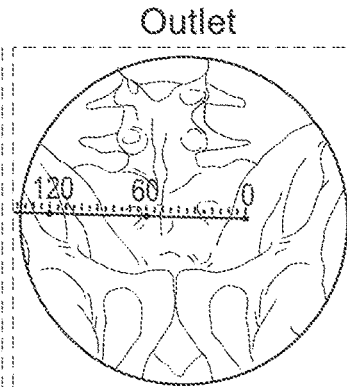
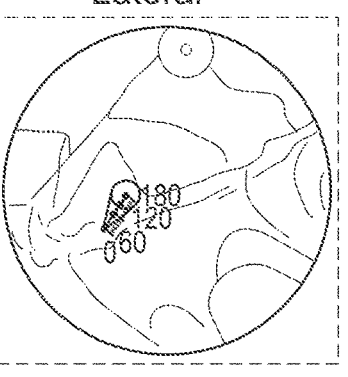
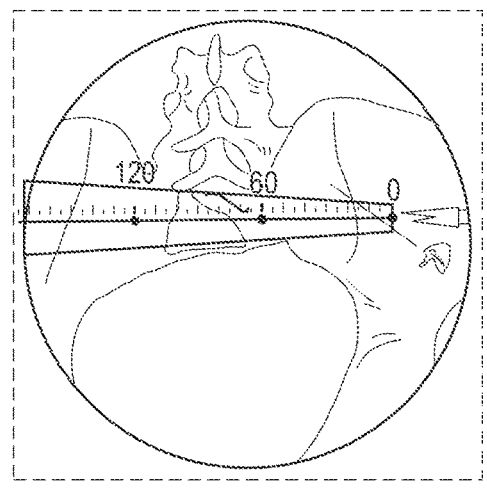
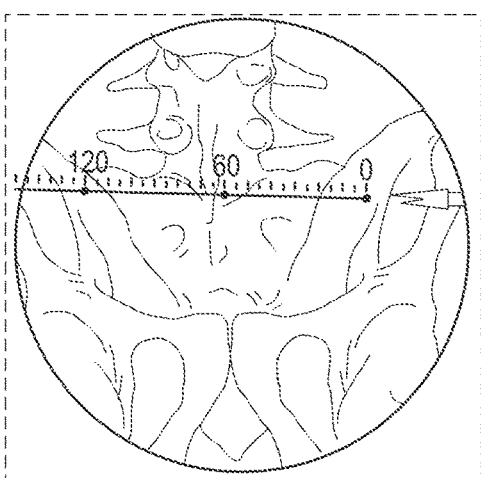
Fig. 19

SURGICAL REFERENCE BODY FOR REFERENCING A PATIENT'S ANATOMY DURING SURGERY

CROSS-REFERENCE TO RELATED APPLICATION

The present application is a national phase entry under 35 U.S.C. § 371 of International Application No. PCT/IB2021/055021, filed on Jun. 8, 2021, all of which is incorporated herein by reference.

FIELD OF THE INVENTION

The present invention relates to a surgical guiding device, a surgical reference body and a surgical tracking system, and in particular to a surgical guiding device, a surgical reference body and a surgical tracking system allowing an improved localization of surgical components, and a corresponding method, computer program product and storage medium having stored thereon the computer program product.

BACKGROUND OF THE INVENTION

Surgical procedures have improved over the recent years. Significant improvements have been achieved by supporting systems for supporting the clinical personal in particular surgeons during surgeries. In particular bone fractures benefit from supporting systems for surgeons, which provide the surgeon with equipment, which allows the surgeon to improve exactness of repositioning of bone parts and positioning of implants, like screws, nails and bone plates, as well as tools and targeting and guiding devices.

As traumatized bones, i.e. fractures, have only a limited visual access, monitoring is usually based on radiating principles, like X-ray imaging or computer tomography CT images, or magnet resonance tomography MRT images. All these principles and methods involve at least one of the drawbacks of being radiation intensive, requiring large devices and requiring a considerable amount of time. Each monitoring step during a surgery prolongs the surgery duration and thus the duration of narcotic impact and increases costs and radiation impact.

Therefore, there is a need for surgical guiding devices, surgical reference bodies and surgical tracking systems as well as corresponding methods, which reduce imaging effort and thus duration of the surgery, reduce radiation impact on the patient, but at the same time maintain or increase the level of exactness of the surgery.

SUMMARY OF THE INVENTION

The present invention provides a surgical guiding device, a surgical reference body and a surgical tracking system, allowing an improved localization and positioning of surgical components, and corresponding methods, computer program products and storage mediums having stored therein the computer program product(s) according the subject matter of the independent claims. Further embodiments are incorporated into the dependent claims.

According to an embodiment of the invention there is provided a surgical reference body for referencing a patient's anatomy during surgery, the surgical reference body comprises: a radio dense geometry having a first radio dense sub-geometry and a second radio dense sub-geometry each being fixedly and spatially reproducibly connected to the surgical reference body; a first leg having an anatomically adapted surface for a patient's anatomy; a second leg having an anatomically adapted surface for a patient's anatomy, wherein the first leg with a first end is connected to a first end of the second leg at a leg joining portion, wherein each of the first radio dense sub-geometry and the second radio dense sub-geometry has a unique radio projection for each proximal to distal orientation of the surgical reference body, so that each of the first radio dense sub-geometry and the second radio dense sub-geometry alone allows determination of the spatial position and orientation of the surgical reference body based on a two dimensional radio projection of at least a part of the surgical reference body.

Thus, it is possible to reduce the focus on the relevant portion of the reference body, in particular when using a larger reference body. Only parts of the reference body may be monitored, while using the respective radio dense sub-geometry for identification. The construction of the legs allows covering a large surface of the patient's anatomy, but allows access between the legs. Such reference body may be used with pelvis surgeries, where the pelvis region requires a reliable referencing by a reference body, which covers large regions of the pelvis. Depending on the viewing direction upon radio imaging, only parts of the entire reference body may be seen in a radio image. Therefore, it is relevant that position and orientation can be determined even if having only a partial view. If providing a plurality of radio dense sub-geometry, each allowing the determination of the spatial position and orientation, it is very likely that at least one of the radio dense sub-geometries is within the imaged portion, and thus allows determination of the position and orientation of the reference body.

According to an embodiment, the first radio dense sub-geometry is allocated to the second end of the first leg and the second radio dense sub-geometry is allocated to the joining portion of the first leg and the second leg.

Thus, if the surgeon orients the first leg of the reference body corresponding to the superior inferior direction of the patient's anatomy, the first radio dense sub-geometry at the second end of the first leg and the second radio dense sub-geometry at the joining portion of the first and second leg, which corresponds to the first end of the first leg, the surgeon can proceed with the two most common imaging directions, inlet and outlet.

According to an embodiment, the surgical reference body further comprises a third radio dense sub-geometry being allocated to the second end of the second leg.

Thus, if the surgeon orients the first leg of the reference body corresponding to the superior inferior direction of the patient's anatomy, the surgeon can proceed not only with the two most common imaging directions, inlet and outlet, but also for the lateral direction.

According to an embodiment, the first leg and the second leg are substantially perpendicular to each other.

Thus, an optimum free space for the surgeon for acting can be provided, which allows sufficient space for the surgery.

According to an embodiment, the first leg and the second leg each have an anatomically adapted surface, which both anatomically adapted surfaces of the first leg and at least a part of the second leg including the first end of the second leg are in a common plane or a uni-dimensionally bent plane.

Thus, the first leg and at least a part of the second leg can be placed on the patient's anatomy, in particular an outer patient's anatomy in the pelvis region. Uni-dimensionally bent plane means an even plane, which is bent in only one direction, like bending a sheet of paper.

According to an embodiment, the first leg and the second leg each have an anatomically adapted surface, which both anatomically adapted surfaces of the first leg and a first part of the second leg including the first end of the second leg are in a common plane or a uni-dimensionally bent plane, wherein have an anatomically adapted surface of a second part of the second leg including the second end of the second leg is inclined with respect to the common plane of the first leg and the first part of the second leg.

Thus, the reference body may be adapted to the bending of the patient's anatomy. Further, the inclined faces support a reliable positioning of the reference body to the patient's anatomy.

According to an embodiment, an inclination plane of the second part of the second leg is substantially parallel to an extension of the first leg.

Thus, the reference body may be better adapted to the bending of the patient's anatomy. Further, the inclined faces support a reliable positioning of the reference body to the patient's anatomy.

According to an embodiment, attached to the second end of the second leg there is provided an optical pattern.

Thus, an optically supported targeting system can be used as described below, without the need for permanent repeated radio imaging.

According to an embodiment, the first radio dense sub-geometry is allocated to the first leg and the second radio dense sub-geometry is allocated to the second leg, and in particular, the first radio dense sub-geometry is allocated to a second end of the first leg and the second radio dense sub-geometry is allocated to a second end of the second leg.

Thus, it is possible to provide a radio dense sub-geometry at each of the legs, so that for each relevant imaging direction a radio dens sub-geometry is within the viewing range so that a determination of the position and orientation can made based on the respective projection of the radio dense sub-geometry.

According to an embodiment there is provided a surgical reference body for referencing a patient's anatomy during surgery, the surgical reference body comprises: a radio dense geometry having a first radio dense sub-geometry, a second radio dense sub-geometry, and a third radio dense sub-geometry each being fixedly and spatially reproducibly connected to the surgical reference body; a first leg having an anatomically adapted surface for a patient's anatomy; a second leg having an anatomically adapted surface for a patient's anatomy, wherein the first leg with a first end is connected to a first end of the second leg at a leg joining portion, wherein each of the first radio dense sub-geometry, the second radio dense sub-geometry, and the third radio dense sub-geometry has a unique radio projection for each proximal to distal orientation of the surgical reference body, so that each of the first radio dense sub-geometry, the second radio dense sub-geometry, and the third radio dense sub-geometry alone allows determination of the spatial position and orientation of the surgical reference body based on a two dimensional radio projection of at least a part of the surgical reference body, wherein the first radio dense sub-geometry is allocated to a second end of the first leg, the second radio dense sub-geometry is allocated to a second end of the second leg, and the third radio dense sub-geometry is allocated to the leg joining portion of the first leg and the second leg.

Thus, with the three radio dense sub-geometries a more distributed arrangement of radio dense sub-geometries can be achieved. This increases a probability that within each taken radio image a projection of a radio dense sub-geometry can be found, which allows determination of the spatial position and orientation of the imaged part.

According to an embodiment, the surgical reference body comprises at least one apex-pin hole.

Thus, it is possible to fix the surgical reference body to a patient's anatomy, so that the spatial position and orientation between the reference body and the patient's anatomy can be established and maintained. It should be noted that it is also possible to provide more than one apex hole. It should be noted that beside one or more apex-pin holes also one or more interfaces may be provided for coupling the optical imaging device or the optical pattern. Such interfaces usually are provided at the surface side facing away from the surface side being used for being adhered to the patient's anatomy.

According to an embodiment the at least one apex-pin hole is located between the first end and the second end of at least one of the first leg and the second leg.

Thus, the apex-pin hole can be provided at a certain distance to the radio dense sub-geometries, if these radio dense sub-geometries are located at the end portions of the leg and at the joining portion of the legs. It should be noted that instead of using an apex pin hole, the reference body may also fixed to patients anatomy via e.g. loops for Velcro attachment, connecting elements for pins or to an additional surgical instrument e.g. with a railway to clamp Hoffmann system.

According to an embodiment at least one of the first leg and the second leg comprises a first sub-leg and a second sub-leg, wherein a first end of the first sub-leg corresponds to the first end of the at least one of the first leg and the second leg, and the second end of the first sub-leg corresponds to the first end of the second sub-leg at a sub-leg joining portion.

Thus, the first and second sub-leg allow an arrangement where the leg trajectory follows a patient's anatomy.

According to an embodiment the sub-leg joining portion comprises at least one of the at least one apex-pin holes.

Thus, the apex hole can be provided at the joining portion of the first and second sub-leg. The joining portion of the first and second sub-leg may correspond to an expose bone of the patient, where the bone is close to the skin, so that an apex-pin can be mounted to the bone of the patient's anatomy.

According to an embodiment an angle between the first leg and the second leg at its joining point is less than 90°, particularly less than 60°.

Thus, a compact framework of legs can be provided. The trajectory of the legs may be bent, the bending may be in a form so as to open the angle.

According to an embodiment an angle between the first sub-leg and the second sub-leg at its joining point is less than 90°, particularly less than 60°.

Thus, a compact framework of legs can be provided. The trajectory of the legs may be bent, the bending may be in a form so as to open the angle.

According to an embodiment the first sub-leg and second sub-leg of one of the first leg and second leg, and the other of the first leg and second leg forms a W-shape.

Thus, the entire reference body may be adapted to the patient's anatomy, in particular the pelvis region of the patient's anatomy. The W-shape allows a stable framework of legs and sub-legs, provides sufficient open space between the legs at the relevant parts of the patient's anatomy and allows a sufficient adoption to the patient's pelvis anatomy, in particular where patient's bones are exposed to be close to the skin surface, which allows a reliable fixing and positional and orientation referencing between the reference body and the patient's anatomy.

According to an embodiment at least a part of the anatomically adapted surfaces comprises an adhering means.

Thus, the reference device may be easily adhered to the patient's anatomy, without additional injury. However, the adhering may also take place in addition to the application to the apex-pin.

According to an embodiment the adhering means comprises a portion, which is a surface portion coated with an adhesive, which is not irritant to human skin.

Thus, the reference body may be easily fixed to the patient's anatomy. The adhesive may be activated or deactivated by applying a particular temperature or radiation.

According to an embodiment, the adhering means comprises a portion, which is one part of a touch fastener, a counterpart thereof is adhereable to human skin.

Thus, the reference body may be easily fixed to the patient's anatomy and upon misalignment, the position of the reference body may be corrected easily.

According to an embodiment, the surgical reference body further comprises a mechanical interface for a mechanical interface of an optical pattern to be coupled so as to form a reproducible relation between the geometry of the surgical reference body and the position and orientation of the optical pattern to be coupled.

Thus, it can be guaranteed that the relative position and orientation of the optical pattern with respect to the connected reference body is established. A positive fit receptacle can be provided for this purpose. This positive fit receptacle can also have a key and keyhole coded portion, which allows connections only for particular combinations, for which the relative position and orientation is known to the system. This may avoid unintended misuse and misinterpretations during operation. The mechanical interface allows to release the unit for selectively re-using of the components.

According to an embodiment, the surgical reference body further comprises an optical pattern so as to form a reproducible relation between the geometry of the surgical reference body and the position and orientation of the optical pattern.

Thus, not only the surgical reference body is provided, but also the optical pattern, to which the surgical reference body is releasable coupled via the interface. It should be noted that the optical pattern also may be integrally formed with the surgical reference body, i.e. is not releasable and does not have a separable interface.

According to an embodiment the optical pattern is composed of a geometrically even raster of light and dark fields, in particular a raster of squared light and dark fields, in particular a raster of light and black fields.

Thus, it is easier to reproduce the orientation and position of the pattern. Further, the printing process is easier to realize and the pattern can be easier calculated. The fields of different colors or shades in the squared raster form a unique pattern area. Geometrically even means that the dimensions of the fields is geometrically even, but each field the can have different colors or shades for forming the unique pattern area.

According to an embodiment the optical pattern is composed of a geometrically even raster of fields of different colors, in particular a raster of squared colored fields, in particular a raster of color gradient fields.

Thus, not only light and dark fields can be used, but also different colors. This allows a color coding which makes it easier for a surgeon to select the right optical pattern. Further when using instead of two options more than two colors, i.e. light and dark, then more information can be stored on the same surface portion. With two options, e.g. light and dark, two fields can reflect four different combinations. With four options, e.g. yellow, blue, red, green, two fields can reflect sixteen different combinations, which is four times more.

According to an embodiment the optical pattern is composed of a honeycomb raster of light and dark fields, in particular a raster of light and dark circles or hexagons in a honeycomb raster, in particular a raster of light and black circles or hexagons.

Thus, a more compact pattern may be provided, as each field of a honeycomb raster is closer to a circle compared to a squared raster. The packing density is higher than with a squared pattern. The fields of different colors or shades in the honeycomb raster form a unique pattern area.

According to an embodiment the optical pattern is composed of a honeycomb raster fields of different colors, in particular a raster of colored circles or hexagons in a honeycomb raster, in particular a raster of color gradient circles or hexagons.

Thus, not only light and dark fields can be used, but also different colors. This allows a color coding which makes it easier for a surgeon to select the right optical pattern. Further when using instead of two options more than two colors, i.e. light and dark, then more information can be stored on the same surface portion. With two options, e.g. light and dark, two fields can reflect four different combinations. With four options, e.g. yellow, blue, red, green, two fields can reflect sixteen different combinations, which is four times more.

According to an embodiment there is provided a method for calibrating a surgical reference body with respect to a patient's anatomy, the method comprises: taking a first image of the surgical reference body as described above to being adhered to a patient's anatomy from a first viewing direction; taking a second image of the surgical reference body according to any one of claims to being adhered to a patient's anatomy from a second viewing direction being different from the first viewing direction; identifying a patient's anatomy and identifying a three-dimensional model of the patient's anatomy based on the first and second image of the surgical reference body and an anatomy database; determining a spatial position and orientation of the surgical reference body with respect to the patient's anatomy based on the radio dense geometry of the surgical reference body; illustrating the three-dimensional model of the patient's anatomy together with a three dimensional illustration of the surgical reference body, seen from a viewing direction, which is selectable by a user.

Thus, the identification of a patient's anatomy based on the two images can be achieved. As both images have one of the radio dense sub-geometries, the spatial position and orientation of the both images can be brought together, as the relative spatial position and orientation of the both radio dense sub-geometries with respect to each other is known. Thus, also the both images can be brought into a positional and orientation relation to each other. Respective anatomies may be provided in a database including a plurality of anatomy models. Anatomy models may be based on a collection of real anatomies, or on algorithms representing anatomies, wherein variations of the anatomies may be achieved by selecting parameters of the algorithm. Identification may take place by comparing the recognized anatomy in the images with corresponding portions of the anatomy stored in a database. The both images do not illustrate all details of the patient's anatomy. However by illustrating or augmenting a three-dimensional model, details which are not present in the both images can be derived from the tree-dimensional model.

According to an embodiment, the method further comprises taking a third image of the surgical reference body as described above to be adhered to a patient's anatomy from a third viewing direction being different from the first viewing direction and the second viewing direction, wherein identifying a patient's anatomy and identifying a three-dimensional model of the patient's anatomy is based on the first, second and third image of the surgical reference body and an anatomy database.

Thus, a more detailed determination and identification of a three-dimensional model may be achieved. The third image may be used for filling details, which are not illustrated in the first and second image. Further, the third image may be used for validating the selection of the identified model.

According to an embodiment, the method further comprises: determining a spatial orientation of a surgical guiding device, having a guiding body and a radio dense geometry being located in a predetermined spatial position and orientation with respect to the guiding body and adapted for providing a unique radio projection for any orientation relative to an imaging device, with respect to the patient's anatomy and the surgical reference body based on the radio dense geometry of the surgical guiding device; and illustrating the three-dimensional model of the patient's anatomy and the three dimensional illustration of the surgical reference body together with a three dimensional illustration of the surgical guiding device, seen from a viewing direction, which is selectable by a user.

Thus, not only the reference body and the anatomy can be visualized, but also a surgical instrument. As the geometry of the surgical instrument usually is known and the anatomy can be identified by the two or three images, and further, the reference body allows determining the relative spatial position and orientation of the items with respect to each other, it is possible to virtually illustrate the entire situation including a surgical instrument, e.g. a guiding tool, even including an item which is guided, i.e. an implant or a further tool, although the guided device is not yet present in the real situation. This allows a real simulation and virtual application of a tool or implant for evaluation whether the planed measures will be successful or at least promising.

According to an embodiment, the method further comprises: determining from a predetermined maximum tolerance of image taking, a predetermined maximum tolerance from identification of patient's anatomy and a predetermined maximum tolerance of determining a spatial position and orientation of the surgical reference body and the surgical guiding device a maximum tolerance along a traveling path of at least one of a surgical implant and a surgical tool to be inserted and guided.

Thus, it can be estimated in how far the tolerances add to each other and in sum probably are larger than the maximum total tolerance. By selecting or adaption one or more parameters, i.e. selecting a different tool or different implant, the surgeon may find a tolerance which is acceptable.

According to an embodiment of the invention, there is provided a computer program product, which when carried out executes the method as describe above.

According to an embodiment of the invention, there is provided a data storage medium having stored thereon an executable code of the computer program product as described above.

It should be noted that the above described embodiments may also be combined and in a combined form provide a synergetic technical effect and synergetic benefits which go beyond the sum of the single technical effects and benefits.

BRIEF DESCRIPTION OF THE FIGURES

The invention will be described by way of the following drawings, which illustrate in FIG. 1: illustrates an exemplary embodiment of a surgical guiding device/surgical instrument/tool in a lateral view.

FIG. 2: illustrates an exemplary embodiment of a surgical guiding device/surgical instrument/tool in a perspective view seen from proximal to distal direction.

FIG. 3: illustrates an exemplary embodiment of a surgical guiding device/surgical instrument/tool in a perspective view seen from proximal to distal direction in a radio image.

FIG. 6: illustrates an exemplary embodiment of a surgical guiding device/surgical instrument/tool having mounted thereon an optical imaging device.

FIG. 7: illustrates an exemplary embodiment of a surgical reference body having a squared optical pattern.

FIG. 8: illustrates an exemplary embodiment of a surgical reference body having a hexagonal optical pattern applied to a patient's anatomy, together with a surgical guiding device/surgical instrument/tool having mounted thereon an optical imaging device.

FIG. 9: illustrates a schematic view of an exemplary embodiment of an image processing device.

FIG. 10: illustrates an exemplary embodiment where the optical imaging device is connected to the surgical tool via respective interfaces and the pattern is connected to the reference body connected via respective interfaces.

FIG. 11: illustrates an exemplary embodiment where the optical imaging device is connected to the reference body via respective interfaces and the pattern is connected to the surgical tool connected via respective interfaces.

FIG. 19 illustrates different application samples of embodiments of the invention.

It should be noted that same or similar reference numerals illustrate same or similar components. Along these Figures exemplary embodiments of the invention will be describes as follows.

DETAILED DESCRIPTION OF EXEMPLARY EMBODIMENTS

Figure 4:
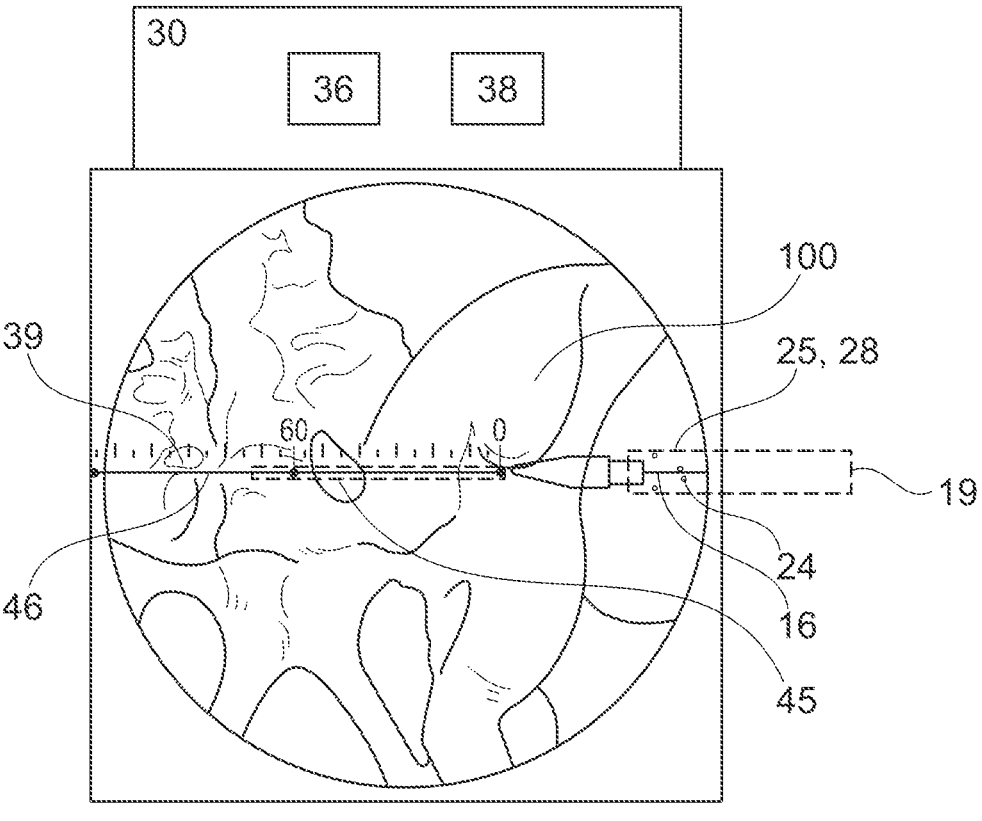
FIG. 4: illustrates a side view in a radio image of a surgical guiding device/surgical instrument/tool applied to a patient's anatomy.

For a surgical implant and a surgical tool, the distal end is defined as the end firstly entered into a patient's body, and the proximal end is defined as the opposite end. For a drilling tool, the end including the drilling geometry is considered as being the distal end and the shaft for fixing the drilling tool to a drilling drive is considered as being the proximal end.

A (radio) projection is considered as projected image of a geometry onto a two-dimensional array.

Complementary patterns of a first and second radio dense sub-geometry are considered as matching patterns, which together form a closed common pattern. Such matching patterns may be formed e.g. by concentric circles or polygons or other shapes having a uniform circumferential distance or overlap, by interleaving segments having a uniform distance or overlap like segments of a circle or polygons or other shapes, etc.

Centre line of a tool, an implant or a part thereof is the imaginary line, which follows a path, which has an equal distance to the lateral edges of the respective tool, implant or part thereof.

Joining point of two legs is considered as the point where the both centerlines of the two legs cross each other or have the smallest distance.

Angle between two legs is considered as an angle defined by a tangent of the centerlines of the respective legs running through a joining point of the both centerlines.

Joining portion of two legs is the area where the both legs toward their joining point are no longer separated, i.e. commonly share their edges.

Complementary patterns of a first and second radio dense sub-geometry are considered as matching patterns, which together form a closed common pattern. Such matching patterns may be formed e.g. by concentric circles or polygons or other shapes having a uniform circumferential distance or overlap, by interleaving segments having a uniform distance or overlap like segments of a circle or polygons or other shapes, etc.

Virtually visualizing a surgical guiding device or a surgical instrument may include a full visualization of the surgical guiding device and surgical instrument, respectively, but in addition or alternatively may also include visualization of a characteristic geometry, which may be an axis of the surgical guiding device and surgical instrument, respectively, and/or a representative scale and/or contour thereof. Virtually visualizing a surgical guiding device or a surgical instrument may also include a visualization of an available variety of implants or the like, e.g. visualizing three different available bone screws, in particular in combination with the patient's anatomy to which a screw is intended to be applied, so that the surgeon may recognize and identify through the virtually visualization the suitable screw out of the variety of screws. It should be noted that this is not limited to the number of three and also not limited to screws, but may also include nails, in particular nails with varying curve radius and other implants and surgical instruments like k-wires and the like.

A unique projection of any intended use orientation of the surgical guiding device or a surgical instrument, does not exclude that a projection of two or more different orientations are identical, as long as the system and/or the surgeon recognizes that the second and each further orientation with identical projection are outside an intended or reasonable use. With this respect a repeated pattern projection may be acceptable, if it always guaranteed, that the orientation within an intended or reasonable use range can be determined based on the unique projection. Outside an intended or reasonable use may be seen if the surgical guiding device or a surgical instrument is upside down oriented or toward an orientation, which cannot lead to serious injuries during surgery.

The correspondence between a reference body and a patient's anatomy can be established by providing a plurality (two or more) images from different positions/orientations (e.g. ML, AP or any other different directions) with the reference body being attached to the patient's anatomy. Based on these plurality of views the relation between the reference body and the patient's anatomy is achieved by image augmentation. The known geometry of a reference body allows determining the scaling of the reference body and the instrument/tool/anatomy in the imaging plane. The different imaging views may be referenced with respect to each other. Further, an automated or manual 2D-image segmentation can be carried out for setting different reference bodies in relation to a patient's anatomy. This can be supported by a database, which includes generally known bone geometries or individually known bone geometries, which can be obtained by e.g. a postoperative CT or the like.

FIG. 1 and FIG. 2 illustrate a surgical guiding system 1 for computer-assisted-surgery CAS. The surgical guiding system 1 comprises a surgical guiding device 10, which is here illustrated as an awl. The surgical guiding device 10 comprises a guiding body 15 having a longitudinal extension from a proximal end 11 of the surgical guiding device to a distal end 12 of the surgical guiding device 10. The guiding body has a hollow shaft 15a, and being adapted for guiding at least one of a longitudinal surgical implant and a longitudinal tool. The surgical implant may be e.g. a screw or a nail or a wire. A tool may be a k-wire, a drill or a needle. The hollow shaft 15a has a guiding channel 15b, wherein the guiding channel follows the guiding trajectory 16 extending along the guiding body and succeeding in distal direction along a traveling path 46 of a surgical implant or a surgical tool to be inserted and guided. The guiding trajectory may be straight or may be bent or curved. A straight trajectory may be used for inserting straight implants or tolls, like a drill or a screw. A bent trajectory may be used for inserting bent or curved implants or tools, like bent nails, or bent wires. The guiding trajectory is to be understood as the trajectory within or on the guiding body 15 or hollow shaft. The traveling path 46 is to be understood as a path extending the guiding path 16 toward the distal direction, i.e. the direction pointing toward the patient. The traveling path usually has a similar curvature as the guiding trajectory 16. If the guiding trajectory 16 is straight, also the traveling path 46 is straight. If the guiding path is curved, usually also the traveling path along which a curved implant or tool is traveling is curved. The traveling path defines the path the guided implant or tool when being inserted travels after exiting the hollow shaft 15a at the distal end, which is here illustrated as the tip 18 of the tool. The here illustrated awl has a handle or knob 17, which is used for handling the awl, in particular for applying a blade at the distal end 12 of the awl. The blade may leave an opening through which a tool or implant may be guided through the hollow shaft and through the distal opening toward the patient.

It should be understood that although FIGS. 1 and 2 illustrate an awl, the guiding device 10 may also be a targeting device for positioning a nail or a screw.

FIG. 2 illustrates at the knob 17 a radio dense geometry 20. The radio dense geometry 20 is located in a predetermined spatial position and orientation with respect to the guiding body 15. The radio dense geometry 20 provides a unique radio projection 25 for any proximal to distal orientation of the guiding body in an intended use orientation of the surgical guiding device 10. As the unique projection allows determining the orientation of the guiding device 10 and thus the guiding body 15 and the hollow shaft 15a, the unique projection can be used for determining the guiding trajectory 16 and the traveling path 46 along which a tool or implant travels when being guided by the hollow shaft 15a. It should be noted that the hollow shaft may also have a lateral slit (not illustrated here) for laterally inserting an implant or tool. This slit may be closed by a cover so as to for a closed hollow shaft 15a. The guiding body (15) comprises a hollow shaft (15a) with a guiding channel (15b), wherein the guiding channel follows the guiding trajectory (16).

The radio dense geometry 20 may have a first radio dense sub-geometry 21 and a second radio dense sub-geometry 22. The first and second radio dense sub-geometries 21, 22 in this illustration are located at the knob 17, but may also be located somewhere on the guiding device 10. Any radio dense geometry 20 or sub-geometry 21, 22, 23 may also be provided as a releasable mounted geometry, e.g. with a clip connection. Sub-geometry 21, 22 may be formed together in a clip. Matching key-keyhole elements on the guiding device and the radio dense geometry 20 or a radio dense sub-geometry 21/22, 23 may establish a predefined orientation and position of the radio dense geometry 20/sub-geometry 21, 22, 23 with respect to the guiding device. The key/keyhole components may also be used that only radio dense geometries 20/sub-geometries 21, 22, 23 which are intended for being used with the guiding device 10 can be clipped to the guiding device. The radio dense geometry may have a unique three-dimensional shape and/or may be composed of sub-geometries together forming the unique projection.

Figure 5:
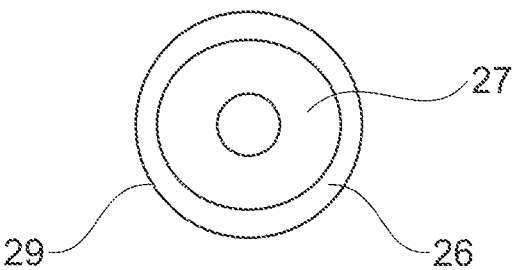
FIG. 5: illustrates a complimentary match of a first and second radio dense sub-geometry.

The first radio dense sub-geometry 21 and the second radio dense sub-geometry 22 may be realized by two circular rings of a radio opaque material, as illustrated in FIG. 2, which are concentrically arranged but not in the same plane but parallel planed. If having a view straight from the proximal to the distal direction, both rings in the projection appear as concentric circles. In this viewing direction the both rings, one of the first radio dense sub-geometry 21 and one of the second radio dense sub-geometry 22 may form a complimentary pattern, here two concentric rings, which may fit into each other. If applying an inclined view from slightly lateral positon, the rings appear as ellipses and no longer concentric. The measure of the concentric shift and the measure of the elliptic deformation, as well as the relative size of the both rings may give a basis for calculating not only the lateral viewing angle, but also the viewing distance. As the geometry of the guiding device is known, also its guiding trajectory 16 is knows and thus the traveling path 46. This applies not only for a straight guiding trajectory, but also to a curved guiding trajectory 16. The radio projection 26 of the first radio dense sub-geometry 21 and the radio projection 27 of the second radio dense sub-geometry 22 together in a predetermined viewing direction, which may be toward the straight longitudinal extension, may have a complementary pattern 29, as illustrated in FIG. 5. This complementary pattern 29 may be formed by e.g. the both concentric rings. Other complementary patterns may be formed by any key/keyhole shapes matching to each other when viewing toward the complementary viewing direction.

As illustrated in FIG. 2 the guiding device may have a further, a third radio dense sub-geometry 23. Whereas the first and second radio dense sub-geometries 21 and 22 in the shown embodiment are located at the proximal end 11 with the knob 17, the third radio dense sub-geometry 23 is located close to the distal end 12 and the tip 18. The third radio dense sub-geometry 23 may be provided with fiducial markers 24, as illustrated in FIG. 4. It should be noted that the third radio dense sub-geometry 23 may also be provided at the proximal end 11 and may also spatially overlap with the first and second radio dense sub-geometries 21 and 22. Fiducial markers 24 may be radio opaque spheres or other geometries, which are spatially arranged so as to commonly provide unique projection for any viewing direction. The concentric circles of the first and second radio dense sub-geometries 21 and 22 may allow a very exact determination of the exact proximal to distal direction, the fiducial markers 24 may allow an exact lateral determination of the spatial orientation.

FIG. 3 illustrates the visualization of the first radio dense sub-geometry 21 with its unique radio projection 26. The radio dense geometry 20, 21, 22, 23 allows a more exact determination as the contour of the guiding device, in particular if the contour of the guiding device is of no high contrast. Based on the position, size and shape of the both rings of the first radio dense sub-geometry 21, it is possible to determine the orientation of the guiding device 10, and to augment and visualize the guiding trajectory 16, as well as the traveling path 46.

The visualization and augmentation can be conducted by an image processing device 30, which may be a computer or any other computational capacity. The image processing device has a visualization means 36 being adapted for a virtual visualization 19 of the orientation of the guiding body 15 with respect to a patient's anatomy 100, based on the unique radio projection 25 of the radio dense geometry 20, here of the third radio dense sub-geometry 23 with its fiducial markers 24, as illustrated in FIG. 4. The unique radio projection 27 of the third radio dense sub-geometry 23, in particular the pattern of the fiducial markers 24, allows a determination of the position and orientation of the guiding device. This allows a virtual visualization 19 of the orientation of the guiding body 15. The image processing device 30 further has an augmenting means 38 for augmenting the guiding trajectory 16 onto the virtual visualization 19 of the orientation of the guiding body 15, so as to visualize a traveling path 46 of at least one of a surgical implant or a surgical tool 45 to be implanted.

In order to simplify the orientation of the surgeon, the augmenting means 38 may augment a reproducible scale 39 along the augmented guiding trajectory 16. This scale 39 may give the surgeon an idea where an implant tip or tool tip will end when being inserted along the guiding trajectory 16. This scale may also support the surgeon in selecting the correct implant/tool length. In combination with an image recognition and anatomy identification, a suggestion may be made t the surgeon which tool or implant is recommended to be used. The augmenting means may also augment a geometry related to an implant to be implanted with respect to a patient's anatomy 100, based on the unique radio projection 25 of the radio dense geometry 20, in particular based on the unique radio projection 27 of the fiducial markers 24 of the third radio dense sub-geometry 23, as illustrated in FIG. 4.

FIGS. 6 and 7 illustrate a surgical tracking system for tracking a surgical instrument 10 with respect to a surgical reference body 50. The surgical tracking system 2 has an optical imaging device 70 and an optical pattern 80. The imaging device 70 takes an image of the pattern 80, and as the pattern has unique portions, the size, distortion and recognized unique pattern portion allows determination of the relative position of the optical imaging device 70 and the pattern 80. The imaging device 70 may be camera or any other image taking device. The imaging device may be coupled to either a surgical tool 10 or a reference body 50 to be attached to a patient's anatomy. The pattern 80 may be coupled to the other of the reference body 50 and the optical imaging device 70. FIG. 5 illustrates that the optical imaging device 70 is coupled to the surgical tool/device 10. FIG. 6 illustrates that the optical pattern 80 is coupled to the reference body 50. Here the pattern 80 is printed directly to the reference body 50. It should be noted that the pattern can also be provided on the surgical instrument/tool 10 side and the optical imaging device 70 may be provided at the reference body 50 side. Both, the pattern 80 and the optical imaging device 70 may be fixedly coupled to the respective instrument 10 and reference body 50, respectively, or may be releasable coupled thereto. It also possible to releasable couple the optical imaging device 70 to the surgical instrument 10, so as to re-use a valuable camera device, whereas the pattern 80 may be un-releasable printed onto the reference body 10, which may be disposed after use.

The imaging device 70, when being mounted to a surgical instrument 10, represents a position and orientation of the surgical instrument 10 with respect to a predetermined viewing direction 71 of the optical imaging device 70), and likewise the optical pattern 80 represents a position and orientation of the surgical reference body 50 with respect to the unique optical sub-pattern 80a. Thus, taking an image from the pattern 80 allows determination of a relative position and orientation of said surgical reference body 50 with respect to the position and orientation of said surgical instrument 10. For this purpose the system is provided with an image processing device 30 having a pattern recognition means 32 and a visualization means 38, as illustrated in FIG. 9. Further the image processing device 30 may have an augmenting means 36.

The image processing device 30 has a pattern recognition means 32 for recognizing the position and orientation of the at least sub-pattern 80a of the optical pattern 80 with respect to a position and viewing direction 71 of the imaging device 70 based on an image taken from the optical imaging device 70 and a stored representation of the optical pattern. Further, the image processing device 30 has a visualization means 38 for virtually visualizing a surgical instrument 10 represented by the optical imaging device 70 and virtually visualizing a surgical reference body 50 represented by the optical pattern 80. Alternatively, the visualization means 38 virtually visualize a surgical instrument 10 represented by the optical pattern 80 and virtually visualize a surgical reference body 50 represented by the optical imaging device 70, depending onto which of the instrument 10 and the reference body 50, the imaging device 70 and the pattern 80 are mounted. If an augmenting means 36 is provided, the augmenting means may augment a moving axis or trajectory of an instrument, a scale or even a virtual instrument or a virtual implant to the visualization. The augmented items may be provided from a conversion process which converts at least two 2-dimensional images to a 3-dimensional image, or from virtually stores items from a data basis. Further, additional information may be augmented, like quantitative scales, implant properties or identifiers etc., which may help the surgeon in identifying the correct measures and items. The augmenting means may augment a predetermined operating trajectory 16, 46 of a surgical instrument 10 onto the virtual visualization of the surgical instrument 10, based on a recognized position and orientation of the at least sub-pattern 80a of the optical pattern 80 with respect to a position and viewing direction 71 of the imaging device 70, so as to visualize an operating path 46 of the surgical instrument 10 relative to a surgical reference body 50 represented by the optical pattern 80. This augmenting may take place on a screen or even in augmenting glasses worn by the surgeon during surgery.

FIG. 10 and FIG. 11 illustrate that the optical imaging device 70 may have a mechanical interface 77a to be coupled to a positive fit receptacle 17a, 57a of one of the surgical instrument 10 and the surgical reference body 50 for forming a unit having a reproducible relation between a geometry of said one of a surgical instrument 10 and a surgical reference body 50, and the position and viewing direction 71 of the optical imaging device 70. Likewise, the optical pattern 80 may comprises a mechanical interface 87a to be coupled to a positive fit mechanical interface 17a, 57a of one of a surgical instrument 10 and a surgical reference body 50 for forming a unit having a reproducible relation between a geometry of said one of a surgical instrument 10 and a surgical reference body 50, and the position and orientation of the optical pattern 80. Instead of providing releasable receptacles, it is also possible to fixedly connect the optical imaging device 70 to one of the surgical instrument 10 and the surgical reference body 50 for forming a unit having a reproducible relation between a geometry of said one of a surgical instrument 10 and a surgical reference body 50, and the position and viewing direction 71 of the optical imaging device 70. Likewise, the optical pattern 80 may fixedly mounted to the other one of a surgical instrument 10 and a surgical reference body 50 for forming a unit having a reproducible relation between a geometry of said one of a surgical instrument 10 and a surgical reference body 50, and the position and orientation of the optical pattern 80.

As illustrated in FIG. 7, the optical pattern 80 is composed of a geometrically even raster 82 of light and dark fields. The fields may be squared or round fields or have a shape which has a certain fit to a rectangular raster. The color of the raster fields may be any differing color, including printing dark or black fields onto a light or white or metallic surface, e.g. an anodized surface of an implant, tool, reference body or the like. In in particular a raster of squared light and dark fields, in particular a raster of light and black field may be used similar to a QR code. Certain anchor patterns may be used for claiming defined sub-patterns. Instead of light and dark or black and white fields, also fields of different color may be used, e.g. red and green, yellow and blue or yellow and black. As an alternative, the optical pattern 80 may be composed of a honeycomb raster 83 of light and dark fields, as illustrated in FIG. 8. The fields may be hexagonal or round fields or have a shape which has a certain fit to a honeycomb raster. The color of the honeycomb raster fields may be any differing color, including printing dark or black fields onto a light or white or metallic surface, e.g. an anodized surface of an implant, tool, reference body or the like. In in particular a raster of squared light and dark fields. Instead of light and dark or black and white fields, also fields of different color may be used, e.g. red and green, yellow and blue or yellow and black.

Figure 12:
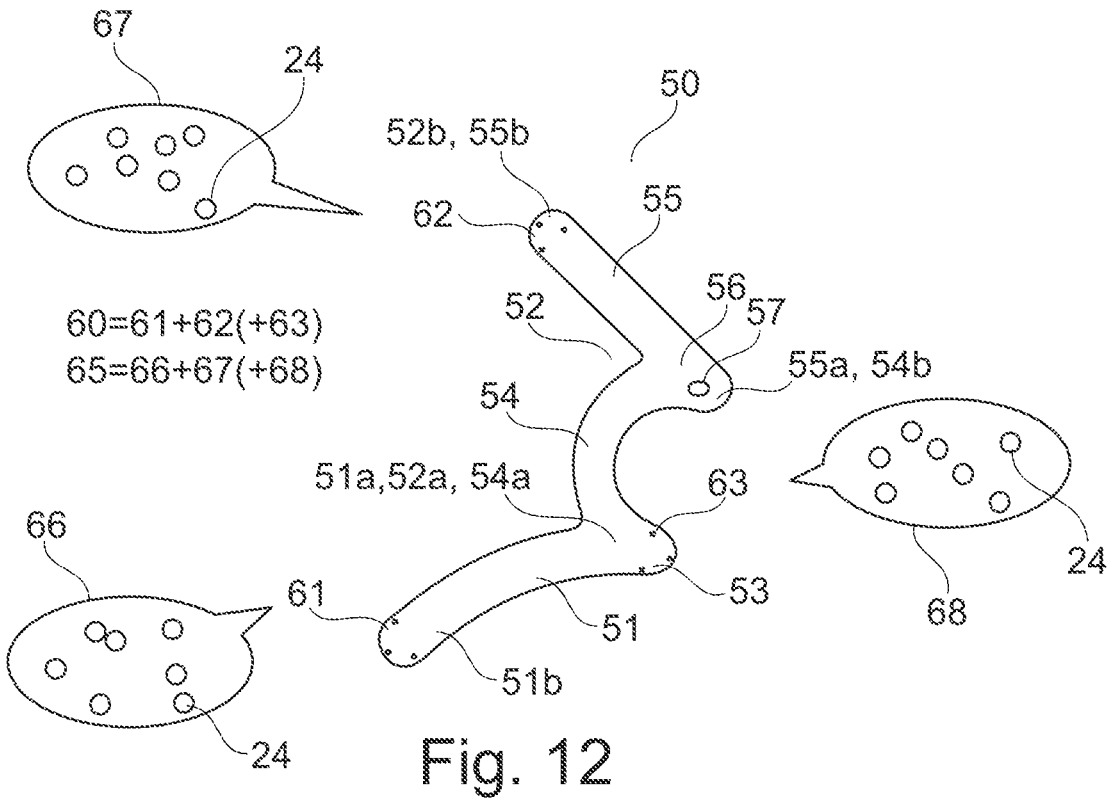
FIG. 12: illustrates an exemplary embodiment of a W-shaped surgical reference body including unique radio projections of the different radio dense sub-geometries.

FIG. 12 illustrates a shape of a surgical reference body 50, which may be aligned to a patient's anatomy 100, as it is illustrated in FIG. 8.

Figure 13:
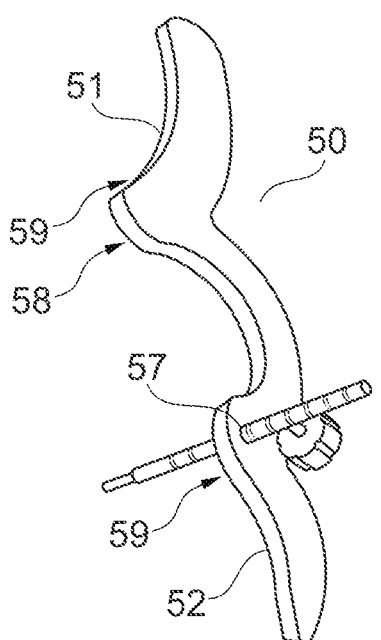
FIG. 13: illustrates an exemplary embodiment of a W-shaped surgical reference body having applied thereto an apex-pin in an apex-pin hole.

The surgical reference body 50 for radio based identification purposes as a radio dense geometry 60 having a first radio dense sub-geometry 61 and a second radio dense sub-geometry 62 each being fixedly and spatially reproducibly connected to the surgical reference body 50. The reference body 50 (which is not illustrated in its general form here) has a first leg 51 and a second leg 52, each having an anatomically adapted surface 59 for a patient's anatomy 100. The anatomically adapted surface is illustrated in FIG. 13. The first leg 51 with a first end 51a is connected to a first end 52a of the second leg 52 at a leg joining portion 53. Each of the first radio dense sub-geometry 61 and the second radio dense sub-geometry 62 has a unique radio projection 66, 67 for each proximal to distal orientation of the surgical reference body 50, so that each of the first radio dense sub-geometry 61 and the second radio dense sub-geometry 62 alone allows determination of the spatial position and orientation of the surgical reference body 50 based on a two dimensional radio projection of at least a part of the surgical reference body. The radio dense geometry may be formed by a set of fiducial markers 24 as described with respect to FIGS. 1 to 4, in particular FIG. 4. The radio dense geometry of the sub-geometries 61, 62 may also be provided by the pattern 80, where e.g. the dark fields of the pattern are made of radio dense material or paint. The first radio dense sub-geometry 61 is allocated to the first leg 51 and the second radio dense sub-geometry 62 is allocated to a second leg 52. In a particular embodiment, the first radio dense sub-geometry 61 is allocated to a second end 51b of the first leg 51 and the second radio dense sub-geometry 62 is allocated to a second end 52b of the second leg 52.

FIG. 12 illustrates a surgical reference body 50 for referencing a patient's anatomy during surgery and having a radio dense geometry 60 having a first radio dense sub-geometry 61, a second radio dense sub-geometry 62, and a third radio dense sub-geometry 63. Each of the sub-geometries is fixedly and spatially reproducibly connected to the surgical reference body 50. The radio dense sub-geometries may be provided as a set of fiducial markers, as illustrated e.g. in FIG. 4, but may also be provided as a raster as illustrated in FIG. 2 or FIG. 3, where e.g. the dark fields are made of a radio dense material and the light fields are not covered by a radio dense material. The first and second leg 51, 52 have an anatomically adapted surface 59 for a patient's anatomy 100, as illustrated in FIG. 8 and FIG. 13. The first leg 51 with a first end 51a is connected to a first end 52a of the second leg 52 at a leg joining portion 53. Each of the first radio dense sub-geometry 61, the second radio dense sub-geometry 62, and the third radio dense sub-geometry 63 has a unique radio projection 66, 67, 68 for each proximal to distal orientation of the surgical reference body 50, so that each of the first radio dense sub-geometry 61, the second radio dense sub-geometry 62, and the third radio dense sub-geometry 63 alone allows determination of the spatial position and orientation of the surgical reference body 50 based on a two dimensional radio projection of at least a part of the surgical reference body. The first radio dense sub-geometry 61 is allocated to a second end 51b of the first leg 51, the second radio dense sub-geometry 62 is allocated to a second end 52b of the second leg 52, and the third radio dense sub-geometry 63 is allocated to the leg joining portion 53 of the first leg 51 and the second leg 52.

FIG. 12 illustrates that the surgical reference body 50 comprises an apex-pin hole 57. The reference body 50 also may have further apex-holes, although not illustrated. The apex-pin hole 57 here is located between the first end 52a and the second end 52b of the second leg 52. As illustrated in FIG. 12, at least one of the first leg 51 and the second leg 52, here in FIG. 12 the second leg 52, is composed of a first sub-leg 54 and a second sub-leg 55, wherein a first end 54a of the first sub-leg 54 corresponds to the first end 52a of the second leg 52, and the second end 54b of the first sub-leg 54 corresponds to the first end 55a of the second sub-leg 55 at a sub-leg joining portion 56. In this illustrated embodiment, the sub-leg joining portion 56 comprises the apex-pin hole 57. The apex-pin hole 57 may receive an apex pin, as illustrated in FIG. 13. The illustrated reference body 50 may have a W-shape, wherein the first sub-leg 54 and second sub-leg 55 of the second leg, and the first leg 51 form the W-shape. For fixing the reference body 50 to a patient's anatomy, the reference body 50 may have on at least a part of the anatomically adapted surfaces 59 an adhering means 58. The adhering means may be a portion, which is a surface portion coated with an adhesive, which is not irritant to human skin. Alternatively or at a different surface portion the adhering means 58 comprises a portion, which is one part of a touch fastener, a counterpart thereof is adhereable to human skin.

Figure 14:
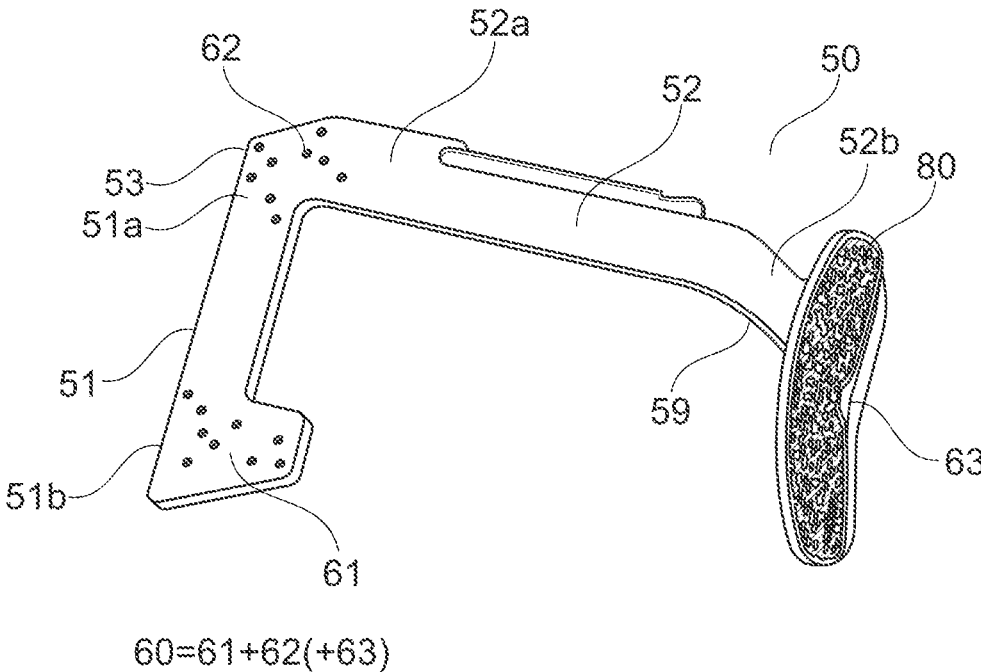
FIG. 14 illustrates another embodiment of a surgical reference body.
Figure 15:
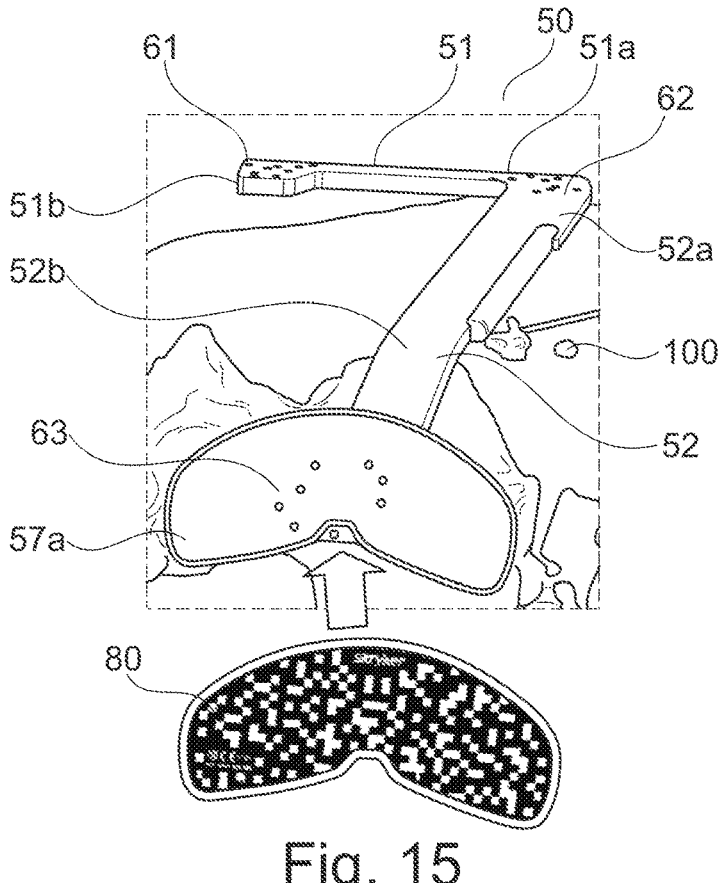
FIG. 15 illustrates a surgical reference body of FIG. 14 applied to a patient's anatomy in a first view.
Figures 16, 17:
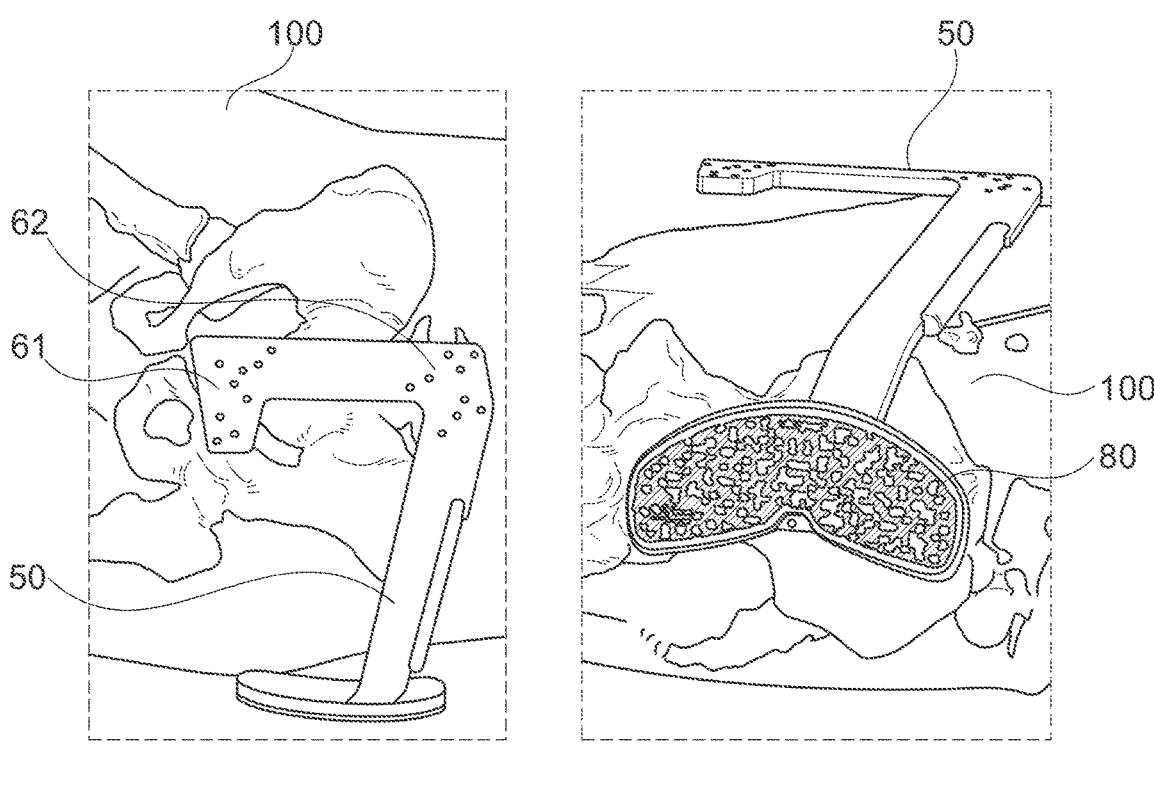
FIG. 16 illustrates a surgical reference body of FIG. 14 applied to a patient's anatomy in a second view.
FIG. 17 illustrates a surgical reference body of FIG. 14 applied to a patient's anatomy in a third view.

FIG. 14 illustrates another embodiment of a surgical reference body 50, which may be aligned to a patient's anatomy 100, as it is illustrated in FIGS. 15, 16 and 17.

The surgical reference body 50 for radio based identification purposes has a radio dense geometry 60 having a first radio dense sub-geometry 61 and a second radio dense sub-geometry 62 each being fixedly and spatially reproducibly connected to the surgical reference body 50. The reference body 50 has a first leg 51 and a second leg 52, each having an anatomically adapted surface 59 for a patient's anatomy 100. The first leg 51 with a first end 51a is connected to a first end 52a of the second leg 52 at a leg joining portion 53. Each of the first radio dense sub-geometry 61 and the second radio dense sub-geometry 62 has a unique radio projection 66, 67 for each proximal to distal orientation of the surgical reference body 50, so that each of the first radio dense sub-geometry 61 and the second radio dense sub-geometry 62 alone allows determination of the spatial position and orientation of the surgical reference body 50 based on a two dimensional radio projection of at least a part of the surgical reference body. The radio dense geometry may be formed by a set of fiducial markers 24 as described with respect to FIGS. 1 to 4, in particular FIG. 4. The first radio dense sub-geometry 61 is allocated to the second end 51b of the first leg 51 and the second radio dense sub-geometry 62 is allocated to a joining portion 53 of the first and second leg, which corresponds to the first end 51a of the first leg 51. Attached to the second end 52b of the second leg 52 may be an optical pattern, the structure and function thereof corresponds to what is described with respect to FIGS. 6 to 8.

FIG. 15 illustrates a surgical reference body 50 for referencing a patient's anatomy 100 during surgery and having a a first radio dense sub-geometry 61, a second radio dense sub-geometry 62, and in this particular embodiment, a third radio dense sub-geometry 63. Each of the sub-geometries are fixedly and spatially reproducibly connected to the surgical reference body 50. The radio dense sub-geometries may be provided as a set of fiducial markers, as illustrated e.g. in FIG. 4. The first and second leg 51, 52 have an anatomically adapted surface 59 for a patient's anatomy 100, as illustrated in FIG. 16 and FIG. 17.

Figure 18:
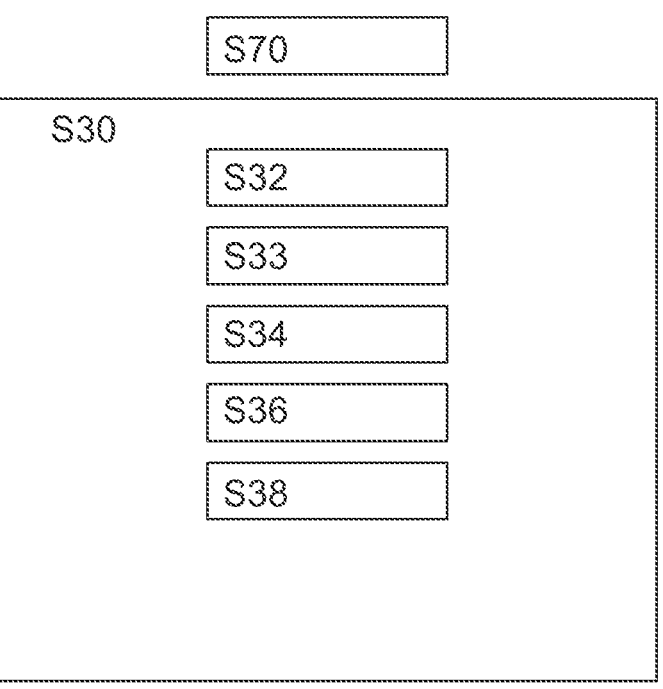
FIG. 18: illustrates an exemplary embodiment of a method with mandatory and optional method steps.

FIG. 18 illustrates a method for assisting positioning an application of implants/tools with respect to a patient's anatomy. The method includes processing imaging S30, which may include recognizing pattern(s) S32 and comparing recognized (sub-)pattern(s) with predetermined pattern (s) S33. Further, processing imaging S30 may include determining position and orientation of (sub-)pattern(s) S34, visualization S36 of the items and augmenting S38 e.g. a guiding trajectory, implant/tool/instrument contours or illustrations. For providing a relative position and orientation of an optical imaging device and an optical pattern, the method may include taking an optical image S70 of the pattern with the imaging device.

REFERENCES 1 surgical guiding system for computer-assisted-surgery CAS
2 surgical tracking system
10 surgical guiding device/surgical instrument
11 proximal end of the surgical guiding device/surgical instrument
12 distal end of the surgical guiding device/surgical instrument
15 guiding body
15a hollow shaft guiding body
15b guiding channel of guiding body
16 guiding trajectory of the guiding body/operating trajectory of surgical instrument
17 knob/handle of surgical guiding device
17a mechanical interface of surgical instrument for optical imaging device or pattern
18 tip of surgical guiding device
18a blade/tool at the tip of surgical guiding device
19 virtual visualization of a guiding body/an orientation of the guiding body
20 radio dense geometry of surgical guiding device
21 first radio dense sub-geometry of surgical guiding device
22 second radio dense sub-geometry of surgical guiding device
23 third radio dense sub-geometry of surgical guiding device
24 fiducial markers
25 radio projection of radio dense geometry of surgical guiding device
26 radio projection of the first sub-geometry of surgical guiding device
27 radio projection of the second sub-geometry of surgical guiding device
28 unique radio projection of the third sub-geometry of surgical guiding device
29 complementary pattern of radio projections of first/second sub-geometry
30 image processing device
32 recognition means for pattern recognition
36 visualization means
38 augmenting means for augmenting the guiding trajectory
39 reproducible scale along augmented guiding trajectory
45 surgical implant/surgical tool
46 traveling path of a surgical implant/surgical tool to be inserted and guided/extended operating trajectory of surgical instrument
50 surgical reference body
51 first leg of surgical reference body
51a first end of first leg
51b second end of first leg
51c center line of first leg
52 second leg of surgical reference body
52a first end of second leg
52b second end of second leg
52c center line of second leg
53 joining portion of first and second leg of surgical reference body
53c joining point of central lines of first/second leg
54 first sub-leg of surgical reference body

54a first end of first sub-leg
54b second end of first sub-leg
54c center line of first sub-leg
55 second sub-leg of surgical reference body
55a first end of second sub-leg
55b second end of second sub-leg
55c center line of second sub-leg
56 joining portion of first and second sub-leg of surgical reference body
56c joining point of central lines of first/second sub-leg
57 fixing hole/apex-pin hole in surgical reference body
57a mechanical interface of surgical reference body for optical imaging device or pattern
58 adhering means of surgical reference body
59 anatomically adapted surface of first/second (sub-)leg
60 radio dense geometry of surgical reference body
61 first radio dense sub-geometry of surgical reference body
62 second radio dense sub-geometry of surgical reference body
63 third radio dense sub-geometry of surgical reference body
64 fiducial markers
65 unique radio projection of radio dense geometry of surgical reference body
66 unique radio projection of the first sub-geometry of surgical reference body
67 unique radio projection of the second sub-geometry of surgical reference body
68 unique radio projection of the third sub-geometry of surgical reference body
70 optical imaging device
71 viewing direction of optical imaging device
77a mechanical interface of optical imaging device for instrument or reference body
80 optical pattern
80a optical sub-pattern
82 even raster of optical pattern
83 honeycomb raster of optical pattern
87a mechanical interface of optical imaging device for instrument or reference body
100 patient's anatomy
S30 processing imaging
S32 recognizing pattern(s)
S33 comparing recognized (sub-)pattern(s) with predetermined pattern(s)
S34 determining position and orientation of (sub-)pattern(s)
S36 visualization
S38 augmenting for augmenting the guiding trajectory
S70 taking optical imaging
The invention claimed is:
1. A surgical reference body for referencing a patient's anatomy during surgery, the surgical reference body comprises:
a radio dense geometry having a first radio dense sub-geometry and a second radio dense sub-geometry each being fixedly and spatially reproducibly connected to the surgical reference body;
a first leg having an anatomically adapted surface for a first portion of anatomy for the patient; and
a second leg having an anatomically adapted surface for a second portion of anatomy for the patient,
wherein the first leg with a first end is connected to a first end of the second leg at a leg joining portion, and the first leg with a second end separate from a second end of the second leg, wherein each of the first radio dense sub-geometry and the second radio dense sub-geometry has a unique radio projection such that each of the first radio dense sub-geometry and the second radio dense sub-geometry alone allows determination of the spatial position and orientation of the surgical reference body based on a two dimensional radio projection of at least a part of the surgical reference body.

2. The surgical reference body of claim 1, wherein the first radio dense sub-geometry is allocated to the second end of the first leg and the second radio dense sub-geometry is allocated to the joining portion of the first leg and the second leg.

3. The surgical reference body of claim 1, further comprising a third radio dense sub-geometry being allocated to the second end of the second leg.

4. The surgical reference body of claim 1, wherein the first leg and the second leg each have an anatomically adapted surface, which both anatomically adapted surfaces of the first leg and at least a part of the second leg including the first end of the second leg are in a common plane or a uni-dimensionally bent plane.

5. The surgical reference body of claim 1, wherein the first leg and the second leg each have an anatomically adapted surface, which both anatomically adapted surfaces of the first leg and a first part of the second leg including the first end of the second leg are in a common plane or a uni-dimensionally bent plane, wherein an anatomically adapted surface of a second part of the second leg including the second end of the second leg is transverse with respect to the common plane of the first leg and the first part of the second leg, wherein an inclination plane of the second part of the second leg is substantially parallel to an extension of the first leg.

6. The surgical reference body of claim 1, wherein the first radio dense sub-geometry is allocated to the first leg and the second radio dense sub-geometry is allocated to the second leg.

7. The surgical reference body of claim 2, wherein the first radio dense sub-geometry is allocated to the second end of the first leg and the second radio dense sub-geometry is allocated to the second end of the second leg.

8. The surgical reference body of claim 1, wherein at least a part of the anatomically adapted surfaces comprises an adhering means.

9. The surgical reference body of claim 1, wherein the adhering means comprises a portion, which is a surface portion coated with an adhesive, which is not irritant to human skin.

10. The surgical reference body of claim 1, wherein the adhering means comprises a portion, which is one part of a touch fastener, a counterpart thereof is adherable to human skin.

11. The surgical reference body of claim 1, further comprising an optical pattern so as to form a reproducible relation between the geometry of the surgical reference body and the position and orientation of the optical pattern.

12. A surgical reference body for referencing a patient's anatomy during surgery, the surgical reference body comprises:
   a radio dense geometry having a first radio dense sub-geometry, a second radio dense sub-geometry, and a third radio dense sub-geometry each being fixedly and spatially reproducibly connected to the surgical reference body;
   a first leg having an anatomically adapted surface for a first portion of anatomy for the patient; and
   a second leg having an anatomically adapted surface for a second portion of anatomy for the patient;
   wherein the first leg with a first end is connected to a first end of the second leg at a leg joining portion, and the first leg with a second end separate from a second end of the second leg,
   wherein each of the first radio dense sub-geometry, the second radio dense sub-geometry, and the third radio dense sub-geometry has a unique radio projection such that each of the first radio dense sub-geometry, the second radio dense sub-geometry, and the third radio dense sub-geometry alone allows determination of the spatial position and orientation of the surgical reference body based on a two dimensional radio projection of at least a part of the surgical reference body,
   wherein the first radio dense sub-geometry is allocated to the second end of the first leg, the second radio dense sub-geometry is allocated to the second end of the second leg, and the third radio dense sub-geometry is allocated to the leg joining portion of the first leg and the second leg.

13. The surgical reference body of claim 12, wherein the surgical reference body comprises at least one apex-pin hole.

14. The surgical reference body of claim 12, wherein the at least one apex-pin hole is located between the first end and the second end of at least one of the first leg and the second leg.

15. The surgical reference body of claim 12, wherein at least one of the first leg and the second leg comprises a first sub-leg and a second sub-leg, wherein a first end of the first sub-leg corresponds to the first end of the at least one of the first leg and the second leg, and the second end of the first sub-leg corresponds to the first end of the second sub-leg at a sub-leg joining portion, wherein the sub-leg joining portion comprises at least one of the at least one apex-pin holes.

16. The surgical reference body of claim 15, wherein the first sub-leg and second sub-leg of one of the first leg and second leg, and the other of the first leg and second leg forms a W-shape.

* * * * *